(12) United States Patent
Hogan

(10) Patent No.: US 9,751,069 B2
(45) Date of Patent: Sep. 5, 2017

(54) COMPOSITIONS AND METHODS FOR ENTRAPPING PROTEIN ON A SURFACE

(71) Applicant: Michael E. Hogan, Tucson, AZ (US)

(72) Inventor: Michael E. Hogan, Tucson, AZ (US)

(73) Assignee: Genomics USA, Inc., Round Rock, TX (US)

( * ) Notice: Subject to any disclaimer, the term of this patent is extended or adjusted under 35 U.S.C. 154(b) by 23 days.

(21) Appl. No.: 14/120,278

(22) Filed: May 14, 2014

(65) Prior Publication Data
US 2014/0342947 A1 Nov. 20, 2014

Related U.S. Application Data

(60) Provisional application No. 61/823,065, filed on May 14, 2013.

(51) Int. Cl.
*B01J 19/12* (2006.01)
*C07K 17/10* (2006.01)
*C07K 17/14* (2006.01)

(52) U.S. Cl.
CPC ............ *B01J 19/123* (2013.01); *C07K 17/10* (2013.01); *C07K 17/14* (2013.01); *B01J 2219/00612* (2013.01); *B01J 2219/00626* (2013.01); *B01J 2219/00637* (2013.01); *B01J 2219/00659* (2013.01); *B01J 2219/00725* (2013.01)

(58) Field of Classification Search
CPC ............................... B01J 19/123; C07K 17/10
USPC .............................................................. 506/9
See application file for complete search history.

(56) References Cited

U.S. PATENT DOCUMENTS

2002/0119465 A1    8/2002   Zhao et al.

FOREIGN PATENT DOCUMENTS

| EP | 1437368 A1 | 7/2004 |
|----|------------|--------|
| EP | 2233925 A1 | 9/2010 |
| WO | 2006062427 A1 | 6/2006 |

*Primary Examiner* — Karla Dines
(74) *Attorney, Agent, or Firm* — Ramey & Schwaller, LLP

(57) ABSTRACT

The present invention provides a formulation to link protein to a solid support that comprises one or more proteins, Oligo-dT and one or more non-volatile, water-soluble protein solvents, solutes or combination thereof in an aqueous solution. Further provided is a method of attaching a protein to a surface of a substrate. The formulations provided herein are contacted onto the substrate surface, printed thereon and air dried. The substrate surface is irradiated with UV light to induce thymidine photochemical crosslinking via the thymidine moieties of the Oligo-dT.

1 Claim, 4 Drawing Sheets

COMPOSITIONS AND METHODS FOR ENTRAPPING PROTEIN ON A SURFACE

CROSS-REFERENCE TO RELATED APPLICATION

This non-provisional application claims benefit of priority under 35 U.S.C. §119(e) of provisional application U.S. Ser. No. 61/823,065, filed May 14, 2013, the entirety of which is hereby incorporated by reference.

BACKGROUND OF THE INVENTION

Field of the Invention

The present invention relates generally to the fields of microarrays and protein chemistry. More specifically, the present invention relates to a formulation and methods for entrapping protein on a surface.

Description of the Related Art

It is well known that proteins may be attached to surfaces, typically by covalent attachment of the protein directly to the solid substrate, or by covalent attachment to polymers that had previously been attached to the surface, or by physical entrapment of the protein into pores within the solid surface itself, or by simple adsorption of the protein to the surface of the microarray. Although such means of attachment allow for a higher concentration of protein, there is a loss in functionality due to chemical modification of the surface. Sol-gels have been used to entrap proteins on solid supports. However, acceptable sol-gels are limited to those without undesirable properties of gelling in the pin during printing, irreproducible spot sizes, cracking, poor adhesion, incompatibility with entrapped components, or reducing activity of the entrapped protein. None of these methods of attachment or entrappment enable site-addressable, self-assembly of a 3 dimensional protein structure on a microarray.

Thus, there is a recognized need in the art for improved formulations and methods for physically entrapping protein on a microarray surface without direct attachment, binding or adsorption to the surface. Specifically, the prior art is deficient in aqueous crosslinkable formulations comprising Oligo-dT and protein(s) that can be entrapped and preserved in a native protein state in a high concentration on the microarray. The present invention fulfills this longstanding need and desire in the art.

SUMMARY OF THE INVENTION

The present invention is directed to a formulation to link protein to a solid support. The formulation comprises one or more proteins, Oligo-dT and one or more non-volatile, water-soluble protein solvents, solutes or combination thereof in an aqueous solution.

The present invention also is directed to a formulation to link protein to a solid support. The formulation comprises one or more proteins, Oligo-dT, and glycerol or glycerol and at least one of sucrose, trehalose or sorbitol in an aqueous solution.

The present invention is directed further to a method of attaching a protein to a surface of a substrate. The method comprises contacting an aqueous formulation containing Oligo dT and a non-volatile, non-aqueous solvent or solute or combination thereof and the protein onto the substrate surface and printing the formulation onto the surface. The substrate surface is air dried and irradiated with UV light to induce thymidine photochemical crosslinking via the thymidine moieties of the Oligo-dT, thereby attaching the protein to the surface of the substrate.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
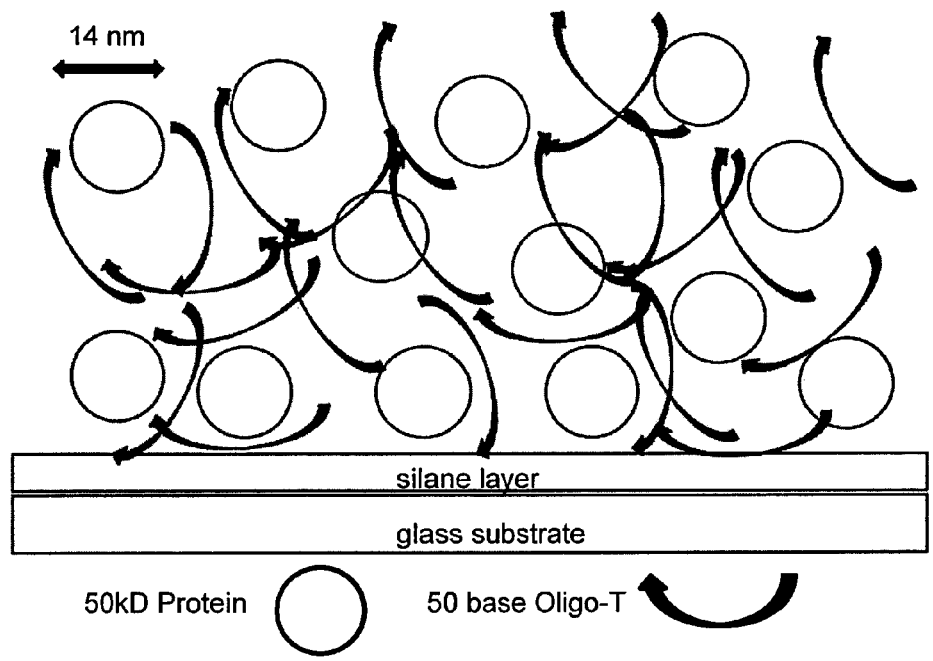
FIG. 1A illustrates photocrosslinking to generate an Oligo-dT+Protein matrix on a microarray surface.

As used herein, the term, "a" or "an" may mean one or more. As used herein in the claim(s), when used in conjunction with the word "comprising", the words "a" or "an" may mean one or more than one. Some embodiments of the invention may consist of or consist essentially of one or more elements, method steps, and/or methods of the invention. It is contemplated that any method, compound, composition, or device described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values, e.g., +/−5-10% of the recited value, that one of ordinary skill in the art would consider equivalent to the recited value, e.g., having the same function or result. In some instances, the term "about" may include numerical values that are rounded to the nearest significant figure.

In one embodiment of the present invention, there is provided a formulation to link protein to a solid support, comprising: one or more proteins; Oligo-dT; and one or more non-volatile, water-soluble protein solvents, solutes or combination thereof in an aqueous solution. In one aspect, the water soluble protein solvent may comprise glycerol or the water soluble protein solvent and solutes may comprise glycerol and at least one of sucrose, trehalose or sorbitol. In this aspect the sucrose, trehalose or sorbitol may be present at a mass ratio of about 0.5:1 up to about 4:1 relative to glycerol. In another aspect, the water soluble protein solvent may comprise propanediol or the water soluble protein solvent and solids may comprise propanediol and at least one of sucrose, trehalose or sorbitol. In this aspect the mass ratio of the sucrose, trehalose or sorbitol is as described supra relative to propanediol. In yet another aspect, the water soluble protein solvents and solids may comprise glycerol and propanediol and at least one of sucrose, trehalose or sorbitol. In yet another aspect, the formulation may be applied to or disposed on a solid support such as an amino-silane layer upon an underlying surface. In this aspect representative underlying surfaces may be, but are not limited to a metal surface, a glass surface or a ceramic surface. In yet another aspect, the formulation may be applied to or disposed on a solid support such as an epoxy-silane layer upon an underlying surface. In this aspect a representative underlying surface is a metal.

In this embodiment and aspects thereof, in the formulation of the present invention, the Oligo-dT may be about 30 bases to about 100 bases in length, preferably about 50 bases long and may be contained in the formulation in a concentration of at least 1 preferably about 1 µg/ml (1 µM) to about 100 µg/ml (100 µM). Also, preferably, the protein may be about 50 kD to 250 kD in mass and may be contained in the formulation in a concentration of at least 10 µg/ml (10 µA). In addition the non-volatile solvent and solutes may be formulated in water at about 1% by mass. Furthermore, representative proteins which may be linked or attached to a surface include, but are not limited to an, immunoglobulin, a glycoprotein, a viral protein, an intact virus, albumin, an HLA, or an enzyme.

In another embodiment of the present invention, there is provided a formulation to link protein to a solid support, comprising one or more proteins; Oligo-dT; and glycerol or glycerol and at least one of sucrose, trehalose or sorbitol in an aqueous solution. In this embodiment the glycerol, sucrose, trehalose and sorbitol may be formulated as described supra. In this embodiment and any aspect thereof, the Oligo-dT size and concentration, the protein size, concentration and type and the solid support all are as described supra.

In yet another embodiment of the present invention, there is provided a method of attaching a protein to a surface of a substrate, comprising the steps of: contacting the aqueous formulation containing Oligo dT and one or more non-volatile, water-soluble protein solvents, solutes or combination thereof and one or more proteins as described herein onto the substrate surface; printing said formulation onto the substrate surface; air-drying the substrate surface; irradiating the substrate surface with UV light to induce thymidine photochemical crosslinking via the thymidine moieties of the Oligo-dT, thereby attaching the protein to the surface of the substrate. In aspects of this embodiment, representative water soluble protein solvents and solutes are as, and may be formulated as, described supra. Also in this embodiment and all aspects thereof, the Oligo-dT size and concentration, the protein size, concentration and type and the solid support all are as described supra.

Described herein are methods and chemical formulations or compositions to link proteins to a solid surface, such as a microarray surface, to generate a biochemical or diagnostic binding assay. The surface attachment is produced by protein entrapment in a polymer network which is formed around the protein, locally, by photo-crosslinking of Oligo-dT, a photoreactive polymer. Oligo-dT, plus one or more proteins and one or more non-volatile, water-soluble solvents and solutes are applied to the solid surface, locally, as a water solution. Upon application of that water solution to the solid surface, the water complement of the solution is allowed to evaporate away, yielding a concentrated, water-depleted phase comprising Oligo-dT, protein, solvents, solutes which is then crosslinked, photochemically, to entrap the protein within the resulting crosslinked, polymeric Oligo-dT network. The non-volatile, water soluble solvents and solutes are chosen so that, subsequent to evaporative water loss, the resulting water-depleted phase remains principally non-crystalline, thereby mitigating protein damage by microcrystal formation. Proteins are linked to an underlying surface, indirectly, rather than by direct chemical linkage to the surface and in a way such that, subsequent to evaporative water depletion and UV crosslinking, the protein becomes entrapped in the crosslinked Oligo-dT network which was created around it. The above combination of indirect photochemical Oligo-dT network entrapment, plus retention of a non-crystalline phase upon water depletion, gives rise to preservation of a native protein state on the solid support, which is then available, subsequent to rehydration, to bind to analytes applied in water solution, as the basis for a binding, or diagnostic or public health screening assay.

More particularly, the Oligo-dT polymer chains are utilized as a linker mediating protein attachment to an underlying microarray surface. Oligo-dT is used a protein surface linker based on its capacity to engage in photocrosslinking. Briefly, Oligo-dT can readily be co-printed in @ 0.5× to 10× mole excess with any number of proteins of interest, e.g., albumin, antibodies, enzymes, HLA or any other water soluble protein. At time of printing, the anionic Oligo-dT adsorbs, non-covalently, to the underlying cationic amino-silane surface via formation of electrostatic bonds. If applied to an epoxysilane coated surface, it can associate with the surface via a combination of covalent linkage to the epoxide and h-bonding to ring opened epoxide diols. The microarray spot is then allowed to air-dry over several minutes. In the present invention, protein printing occurs with one of several water-soluble (but non-volatile) solutes, in a buffered water solution, which upon air drying, becomes a water-depleted fluid, which retains solubilization of the protein and eliminates buffer salt crystal formation, which would have occurred if the water-soluble non-aqueous solutes were not added.

Several solutes and solute mixtures can be used, such as for example, including but not limited to glycerol; Glycerol with propanediol; propanediol; glycerol with sorbitol; glycerol with propane diol and sorbitol; propanediol and sorbitol; glycerol with trehalose; glycerol with propane diol and trehalose; and propanediol and trehalose. Protein can be printed at one of several concentrations (250 ug/ml-5 ug/ml); 500 ug/ml; 250 ug/ml; 100 ug/ml; 50 ug/ml; 20 ug/ml; and 10 ug/ml.

Figure 1B:
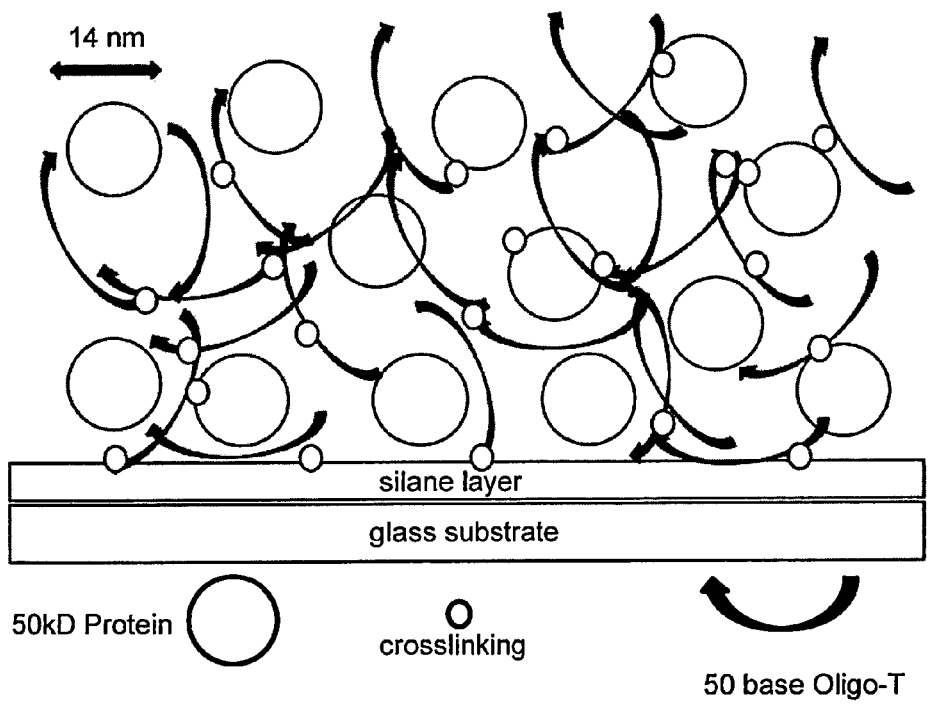
FIG. 1B illustrates the Oligo-dT+Protein matrix of FIG. 1A after UV crosslinking.

In all cases, after printing and air-drying, the resulting microarrays (FIG. 1A) can be subjected to standard UV-Crosslinking at @300 mjoule, to photo-crosslink link the Oligo-dT (via T-T bonding) into a loosely-crosslinked matrix and in some cases to covalently link some of the protein to one or more nearby Oligo-dT molecules in the locally-generated Oligo-dT matrix (FIG. 1B)

Subsequent to UV crosslinking, the microarray is then ready for use. Standard binding steps can be employed: to be performed at lab ambient temperature or at elevated temperature: (1) Prebinding: Ordinary buffered solution with a blocking agent to obscure unused surface sites; (2) Binding: Ordinary buffered solution with a blocking agent to obscure unused surface sites; (3) Washing: Ordinary buffered solution with a blocking agent to obscure unused surface sites; and/or (4) Dry and Image.

As would be immediately recognizable to a person having ordinary skill in this art, the formulations and methods of the present invention may be used to fabricate a protein microarray via contact, or piezoelectric or ink jet printing onto a suitable solid support or to fabricate a protein biosensor via contact. Alternatively, the formulation when placed in contact with an aqueous biological sample, the microarray may be used as an in vitro diagnostic test or when placed in contact with an aqueous biological sample, the biosensor is used as an in vitro diagnostic test.

The following examples are given for the purpose of illustrating various embodiments of the invention and are not meant to limit the present invention in any fashion.

EXAMPLE 1

Structure of a Representative Microarray, to be Printed for the Purposes of Testing Oligo-dT Entrapment of Protein on a Microarray Surface A single protein, for example, bovine albumin, can be printed to form a microarray. Each spot in the microarray can differ in the protein concentration, the Oligo-dT concentration and the water soluble, non-volatile solute to be added (at @1% by mass) at time of printing. Buffer concentration can be as needed, but 2 mM $Na_2Phos$, pH 8.4 is representative.

TABLE I

Formulation of the individual microarray spots to vary Protein, Oligo-dT and Solvent composition in a 12 × 12 microarray

| | Left 6 × 13 segment of 12 × 12 Microarray | | | | | |
|---|---|---|---|---|---|---|
| Protein conc | 250 ug/ml | 250 ug/ml | 100 ug/ml | 100 ug/ml | 50 ug/ml | 50 ug/ml |
| OligoT | 50-mer 100 uM Glycerol | 50-mer 100 uM Glycerol | 50-mer 100 uM Glycerol | 50-mer 100 uM Glycerol | 50-mer 100 uM Glycerol | 50-mer 100 uM Glycerol |
| OligoT | 50-mer 50 uM Glycerol | 50-mer 50 uM Glycerol | 50-mer 50 uM Glycerol | 50-mer 50 uM Glycerol | 50-mer 50 uM Glycerol | 50-mer 50 uM Glycerol |
| OligoT | 50-mer 25 uM Glycerol | 50-mer 25 uM Glycerol | 50-mer 25 uM Glycerol | 50-mer 25 uM Glycerol | 50-mer 25 uM Glycerol | 50-mer 25 uM Glycerol |
| OligoT | 50-mer 100 uM G-PD | 50-mer 100 uM G-PD | 50-mer 100 uM G-PD | 50-mer 100 uM G-PD | 50-mer 100 uM G-PD | 50-mer 100 uM G-PD |
| OligoT | 50-mer 50 uM G-PD | 50-mer 50 uM G-PD | 50-mer 50 uM G-PD | 50-mer 50 uM G-PD | 50-mer 50 uM G-PD | 50-mer 50 uM G-PD |
| OligoT | 50-mer 25 uM G-PD | 50-mer 25 uM G-PD | 50-mer 25 uM G-PD | 50-mer 25 uM G-PD | 50-mer 25 uM G-PD | 50-mer 25 uM G-PD |
| OligoT | 50-mer 100 uM PD | 50-mer 100 uM PD | 50-mer 100 uM PD | 50-mer 100 uM PD | 50-mer 100 uM PD | 50-mer 100 uM PD |
| OligoT | 50-mer 50 uM PD | 50-mer 50 uM PD | 50-mer 50 uM PD | 50-mer 50 uM PD | 50-mer 50 uM PD | 50-mer 50 uM PD |
| OligoT | 50-mer 25 uM PD | 50-mer 25 uM PD | 50-mer 25 uM PD | 50-mer 25 uM PD | 50-mer 25 uM PD | 50-mer 25 uM PD |
| OligoT | 50-mer 100 uM Trehalose | 50-mer 100 uM Trehalose | 50-mer 100 uM Trehalose | 50-mer 100 uM Trehalose | 50-mer 100 uM Trehalose | 50-mer 100 uM Trehalose |
| OligoT | 50-mer 50 uM Trehalose | 50-mer 50 uM Trehalose | 50-mer 50 uM Trehalose | 50-mer 50 uM Trehalose | 50-mer 50 uM Trehalose | 50-mer 50 uM Trehalose |
| OligoT | 50-mer 25 uM Trehalose | 50-mer 25 uM Trehalose | 50-mer 25 uM Trehalose | 50-mer 25 uM Trehalose | 50-mer 25 uM Trehalose | 50-mer 25 uM Trehalose |
| | Right 6 × 13 segment of 12 × 12 Microarray | | | | | |
| Protein conc | 20 ug/ml | 20 ug/ml | 10 ug/ml | 10 ug/ml | 5 ug/ml | 5 ug/ml |
| OligoT | 50-mer 100 uM Glycerol | 50-mer 100 uM Glycerol | 50-mer 100 uM Glycerol | 50-mer 100 uM Glycerol | 50-mer 100 uM Glycerol | 50-mer 100 uM Glycerol |
| OligoT | 50-mer 50 uM Glycerol | 50-mer 50 uM Glycerol | 50-mer 50 uM Glycerol | 50-mer 50 uM Glycerol | 50-mer 50 uM Glycerol | 50-mer 50 uM Glycerol |

TABLE I-continued

Formulation of the individual microarray spots to vary Protein, Oligo-dT and Solvent composition in a 12 × 12 microarray

| OligoT | 50-mer | 50-mer | 50-mer | 50-mer | 50-mer | 50-mer |
|---|---|---|---|---|---|---|
|  | 25 uM | 25 uM | 25 uM | 25 uM | 25 uM | 25 uM |
|  | Glycerol | Glycerol | Glycerol | Glycerol | Glycerol | Glycerol |
| OligoT | 50-mer | 50-mer | 50-mer | 50-mer | 50-mer | 50-mer |
|  | 100 uM | 100 uM | 100 uM | 100 uM | 100 uM | 100 uM |
|  | G-PD | G-PD | G-PD | G-PD | G-PD | G-PD |
| OligoT | 50-mer | 50-mer | 50-mer | 50-mer | 50-mer | 50-mer |
|  | 50 uM | 50 uM | 50 uM | 50 uM | 50 uM | 50 uM |
|  | G-PD | G-PD | G-PD | G-PD | G-PD | G-PD |
| OligoT | 50-mer | 50-mer | 50-mer | 50-mer | 50-mer | 50-mer |
|  | 25 uM | 25 uM | 25 uM | 25 uM | 25 uM | 25 uM |
|  | G-PD | G-PD | G-PD | G-PD | G-PD | G-PD |
| OligoT | 50-mer | 50-mer | 50-mer | 50-mer | 50-mer | 50-mer |
|  | 100 uM | 100 uM | 100 uM | 100 uM | 100 uM | 100 uM |
|  | PD | PD | PD | PD | PD | PD |
| OligoT | 50-mer | 50-mer | 50-mer | 50-mer | 50-mer | 50-mer |
|  | 50 uM | 50 uM | 50 uM | 50 uM | 50 uM | 50 uM |
|  | PD | PD | PD | PD | PD | PD |
| OligoT | 50-mer | 50-mer | 50-mer | 50-mer | 50-mer | 50-mer |
|  | 25 uM | 25 uM | 25 uM | 25 uM | 25 uM | 25 uM |
|  | PD | PD | PD | PD | PD | PD |
| OligoT | 50-mer | 50-mer | 50-mer | 50-mer | 50-mer | 50-mer |
|  | 100 uM | 100 uM | 100 uM | 100 uM | 100 uM | 100 uM |
|  | Trehalose | Trehalose | Trehalose | Trehalose | Trehalose | Trehalose |
| OligoT | 50-mer | 50-mer | 50-mer | 50-mer | 50-mer | 50-mer |
|  | 50 uM | 50 uM | 50 uM | 50 uM | 50 uM | 50 uM |
|  | Trehalose | Trehalose | Trehalose | Trehalose | Trehalose | Trehalose |
| OligoT | 50-mer | 50-mer | 50-mer | 50-mer | 50-mer | 50-mer |
|  | 25 uM | 25 uM | 25 uM | 25 uM | 25 uM | 25 uM |
|  | Trehalose | Trehalose | Trehalose | Trehalose | Trehalose | Trehalose |
| OligoT | 20 ug/ml | 20 ug/ml | 10 ug/ml | 10 ug/ml | 5 ug/ml | 5 ug/ml |

Glycerol: Glycerol at 1% by mass; G-P: Glycerol-1,2Propanediol 1:1 at 1% by mass; PD: 1,2Propanediol at 1% by mass; Trehalose: Trehalose at 1% by mass

EXAMPLE 2

Quantitative Considerations: Addition of Oligo-dT & Protein Prior to Crosslinking on the Microarray Surface It is well known that nucleic acid strands, especially those rich in thymidine, such as a simple repeating DNA oligomer dTn, i.e. Oligo-dT, become photochemically crosslinked to one another upon irradiation in the 250 nm to 230 nm range, due to photochemical excitation of the thymidine ring, followed by addition to the C4-C5 bond of another T or C: or if in proximity, to a nearby protein, especially lysine or cysteine side chains or aromatic amino acid side chains tyrosine or tryptophan. The present invention exploits the photochemistry of Oligo-dT, or Oligo-U if an RNA oligomer, to create within a microarray spot, local formation of a crosslinked Oligo-dT (Oligo-U) matrix which can physically entrap proteins which are applied along with Oligo-dT at time of microarray printing and before UV crosslinking (FIGS. 1A-1B).

Water soluble proteins in the 50 kD to 250 kD range are typically 10 nm to 20 nm in diameter. One can for example, employ bovine albumin, which has a mass of 67 kD and a measured nearly spherical radius of 7 nm. The rise per repeat of single stranded nucleic acids is @0.5 nm per base. Consequently a 50 base long Oligo-dT molecule would present a total contour length of @25 nm, roughly 2× the diameter of the albumin.

If Oligo-dT were mixed in molar excess with a protein such as albumin, in a water solution that contained about 1% of a water-soluble fluid solute, like glycerol, propanol, or glycerol-propanediol, or a water soluble solid solute such as trehalose or sucrose or sorbitol, then allowed to air-dry to evaporate away the water in it, the resulting water-depleted phase will concentrate the protein and Oligo-dT molecules in it about 100-fold. Below, several calculations are displayed for the result of such concentration, for a representative 50 kd protein with a diameter of 14 nm which is similar to a globular protein such as bovine albumin.

Microarray fabrication, of the kind to be exploited in the present invention is a type of nanotechnology, where individual microarray elements or "spots" are applied to a surface as nanoliter droplets, which typically form spots on a surface that are about 100 microns in diameter. The present invention describes by calculation, the effect of depositing a typical 1 nanoliter droplet on a microarray surface, under conditions such that, as described above, air drying of the water in it will cause non-volatile solutes, such as glycerol, or propanediol alone or with solids like trehalose or sorbitol, to be concentrated 100-fold within the 100 um spot, thereby reducing the thickness of the spot.

Microarray Spot Fluid Thickness Calculation: Subsequent to Air-Drying

Assume $1 \times 10^{-9}$ L print volume=$1 \times 10^{-6}$ cm$^3$.
Assume 100-fold air-drying to $1 \times 10^{-11}$ L=$1 \times 10^{-8}$ cm$^3$.
Assume Spot Diameter=$1 \times 10^{-2}$ cm (100 um).
Spot Area=$1 \times 10^{-4}$ cm$^2$
Film Thickness=Print Volume after Air-Drying/Spot Area=[$1 \times 10^{-8}$ cm$^3$]/$1 \times 10^{-4}$ cm$^2$=$1 \times 10^{-4}$ cm=1 um Assuming 1 nL print of 1% non-volatile solutes:
Final Spot Shape upon 100-fold evaporative concentration.
Spot Width=100 um and Spot Thickness=1 um
Surface Coverage Calculations
1). Assuming that a Protein is @14 nm in diameter, its 2D projection=150 nm$^2$.
2). If the Microarray spot is 100 um wide, its area=$0.75 \times 10^{-8}$ m$^2$=$75 \times 10^{+9}$ nm$^2$.

3). So one 100 um spot will be covered by @$0.5 \times 10^{+8}$ Protein molecules, as a one-molecule thick layer 4). If contact print volume=1 nL, at:
- 5 uM=$3 \times 10^{+9}$ molecules per spot yields 30 molecule deep Protein layer, post evaporation;
- 2 uM=$1.5 \times 10^{+9}$ molecules per spot yields 12 molecule deep Protein layer, post evaporation;
- 1 uM=$0.75 \times 10^{+9}$ molecules per spot yields 1.5 molecule deep Protein layer, post evaporation;
- 0.4 uM=$0.3 \times 10^{+9}$ molecules per spot yields 0.6 molecule deep Protein layer, post evaporation;
- 0.2 uM=$0.15 \times 10^{+9}$ molecules per spot yields 0.3 molecule deep Protein layer, post evaporation; and
- 0.1 uM=$0.08 \times 10^{+9}$ molecules per spot yields 0.15 molecule deep Protein layer, post evaporation.

TABLE IIa

Protein and Oligo-dT concentration subsequent to air-drying at 1% of non-volatile solute to affect a controlled 100-fold volume decrease

| Protein Print Concentration | Protein Print Concentration | Concentration After Drying 100-Fold | Average Protein-Protein Molecular Separation Upon Drying |
|---|---|---|---|
| 250 µg/ml | 5 µM | 500 µM | 75 nm |
| 100 µg/ml | 2 µM | 200 µM | 100 nm |
| 50 µg/ml | 1 µM | 100 µM | 130 nm |
| 20 µg/ml | 0.4 µM | 40 µM | 170 nm |
| 10 µg/ml | 0.2 µM | 20 µM | 220 nm |
| 5 µg/ml | 0.1 µM | 10 µM | 270 nm |

TABLE IIb

Oligo-dT concentration subsequent to air-drying at 1% of non-volatile solute (100-fold volume decrease)

| Oligo-dT Print Concentration | Concentration After Drying 100-Fold | Average Molecular Separation Upon Drying |
|---|---|---|
| 100 µM | 10 mM | 28 nm |
| 50 µM | 5 mM | 35 nm |
| 25 µM | 2.5 mM | 44 nm |
| 10 µM | 1.0 mM | 60 nm |
| 2 µM | 0.2 mM | 100 nm |
| 1 µM | 0.1 mM | 130 nm |

The calculations in Table IIa and Table IIb suggest that in an ordinary microarray spot that is @100 um in diameter, containing 1% by volume of a non-volatile, water miscible solvent (like glycerol or propanediol or non-volatile water-soluble solutes such as trehalose or sorbitol) ordinary air-drying will result in a spot that is about 1 um thick. The calculations also show that if a @50 kD protein is printed at @250 ug/ml, the average separation between 14 nm wide protein molecules will be reduced by concentration to @75 nm, or about 5× the protein diameter (FIG. 1A). If printed at @10 uM, Oligo-dT will also concentrate 100 fold, to yield an average separation of only about 60 nm, or about 4× the diameter of the protein, thus yielding a dense network of Oligo-dT molecules surrounding the protein molecules between them (FIG. 1A). If desired, the effective pore size of the Oligo-dT network could be increased to an average separation of 100 nm if the Oligo-dT were applied at 2 uM prior to 100-fold air dying, or conversely, if the Oligo-dT were applied at 50 uM, in the original water-containing phase the pore size upon drying could be reduced to about 35 nm.

While still water-free, due to the dense proximity of Oligo-dT strands, photochemical crosslinking will be efficient: between Oligo-dT strands and also between Oligo-dT and the protein (FIG. 1B). Interestingly, at 250 ug/ml, the same calculation suggest that protein molecules will on average "pile" to form a layer on the microarray surface that is about 12 protein molecules deep within the water depleted, 1 um thick microarray spot. Thus, FIG. 1B represents about 200 um (about $\frac{1}{5}^{th}$) of such a 1 um-thick desiccated microarray spot. Upon rehydration of that 1 um thick Oligo-dT+protein layer, wetting will cause the layer to swell, the separation between protein molecules to increase, thus preparing the protein, while still entrapped in the crosslinked Oligo-dT matrix, for subsequent microarray-based binding interaction with water-soluble analytes of interest.

EXAMPLE 3

Protein Attachment to Solid Surfaces

The present invention is novel in that protein is not linked to the surface directly, nor to a preformed polymer field, or to pores in the solid support or by adsorption to the microarray surface. Instead, the protein is applied to the microarray surface with Oligo-dT, which although not a high polymer, forms an extended polymeric matrix within a microarray spot, subsequent to controlled evaporative concentration, followed by photochemical crosslinking.

The physical and chemical entrapment of protein within that Oligo-dT matrix is created locally, only within the spots comprising sites of microarray fluid deposition, thereby allowing site-addressable, self-assembly of a 3 dimensional protein structure such as that in FIGS. 1A-1B. The key components of the invention are the length of the Oligo-dT (typically @50 bases), the ratio of Oligo-dT to protein (typically 1/1 to 10/1 on a mole basis), and the ability to control the final concentration of protein and Oligo-dT after ordinary evaporation, by including water-miscible, non-volatile solvents and solutes, typically at 1% by mass, so that the protein & Oligo-dT will concentrate @ 100-fold prior to UV crosslinking.

A number of such water-soluble non-volatile solvents and solutes may be used, but they must all share the property that, upon evaporative water loss, and, importantly, protein remains soluble and in a stable folded form, i.e., does not denature, in the water-depleted state. There are several such solvents and solutes of that kind, including glycerol, propanediol, butanediol, trehalose, sorbitol, sucrose and mixtures thereof which are known to retain protein folding even when the protein remains in them with little to no added water.

A Bovine Serum Albumin Microarray

The present invention describes using bovine serum albumin (BSA) as the protein in a microarray. This BSA has been produced with a biotin modification, so that streptavidin phycoerythrin (SAPE) can bind to the biotin of it, and after imaging of the green PE fluorescence (532 nm) serve to localize the BSA protein on the microarray surface. The BSA is applied to the surface as a solution with CY-5 labelled Oligo dT (50 bases long) along with an excess of unlabeled Oligo-dT (50 bases long) which may be imaged via the red CY-5 fluorescence (635 nm). Table III provides a detailed composition of that microarray.

TABLE III

Figure 2A:
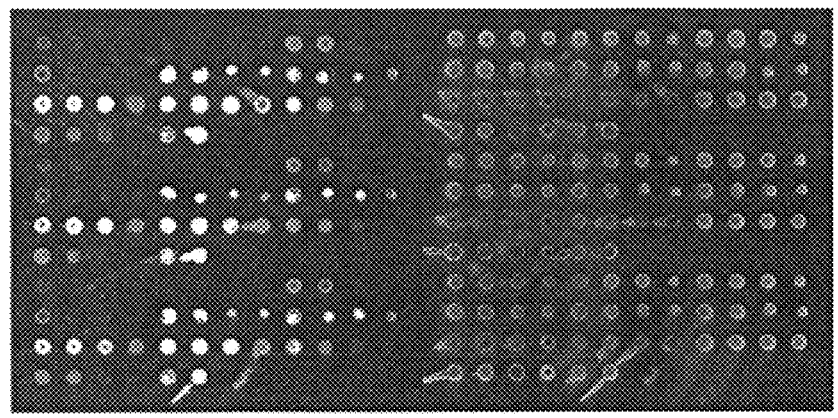
FIG. 2A is a fluorescent microarray image of a bovine serum albumin (BSA) microarray on an amino silane surface.
Figure 2B:
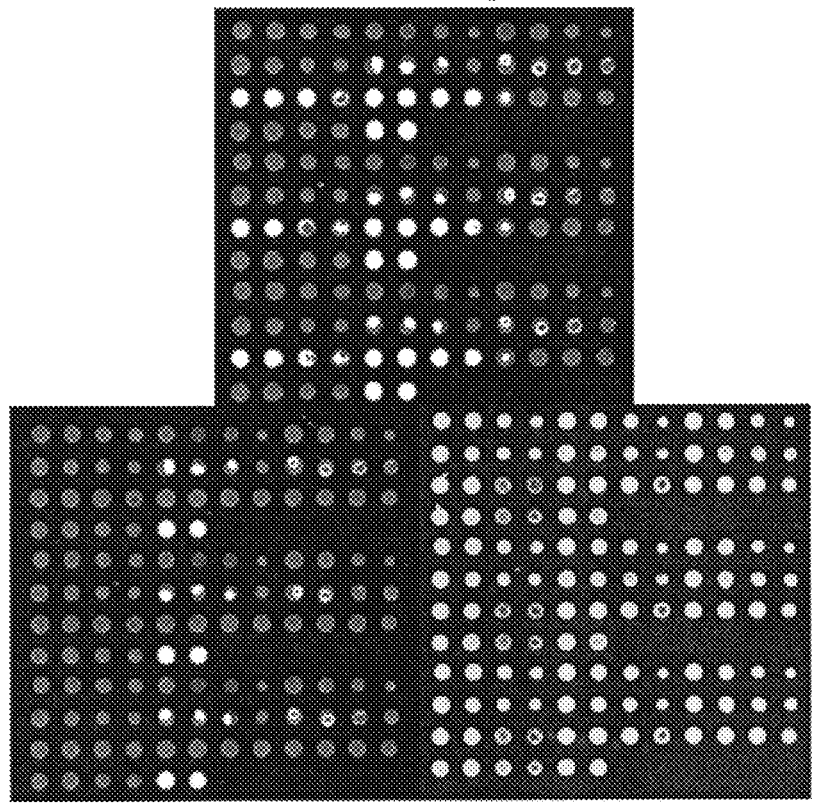
FIG. 2B is a fluorescent microarray image of a BSA microarray on an epoxy silane surface.

Bovine Serum Albumin (BSA) microarray design to yield data in FIGS. 2A-2B

Left 6 × 13 segment of 12 × 12 Microarray

| [BSA] conc | 250 µg/ml | 100 µg/ml | 50 µg/ml | 20 µg/ml | 250 µg/ml | 100 µg/ml |
|---|---|---|---|---|---|---|
| OligoT | 50-mer 100 µM glycerol | 50-mer 100 µM glycerol | 50-mer 100 µM glycerol | 50-mer 100 µM glycerol | 50-mer 25 µM glycerol | 50-mer 25 µM glycerol |
| OligoT | 50-mer 25 µM G-PD | 50-mer 25 µM G-PD | 50-mer 25 µM G-PD | 50-mer 25 µM G-PD | 50-mer 100 µM G-PD | 50-mer 100 µM G-PD |
| OligoT | 50-mer 100 µM trehalose | 50-mer 100 µM trehalose | 50-mer 100 µM trehalose | 50-mer 100 µM trehalose | 50-mer 25 µM trehalose | 50-mer 25 µM trehalose |
| OligoT | 50-mer 25 µM G-S | 50-mer 25 µM G-S | 50-mer 25 µM G-S | 50-mer 25 µM G-S | 50-mer control | 50-mer control |
| OligoT | 50-mer 100 µM glycerol | 50-mer 100 µM glycerol | 50-mer 100 µM glycerol | 50-mer 100 µM glycerol | 50-mer 25 µM glycerol | 50-mer 25 µM glycerol |
| OligoT | 50-mer 25 µM G-PD | 50-mer 25 µM G-PD | 50-mer 25 µM G-PD | 50-mer 25 µM G-PD | 50-mer 100 µM G-PD | 50-mer 100 µM G-PD |
| OligoT | 50-mer 100 µM trehalose | 50-mer 100 µM trehalose | 50-mer 100 µM trehalose | 50-mer 100 µM trehalose | 50-mer 25 µM trehalose | 50-mer 25 µM trehalose |
| OligoT | 50-mer 25 µM G-S | 50-mer 25 µM G-S | 50-mer 25 µM G-S | 50-mer 25 µM G-S | 50-mer control | 50-mer control |
| OligoT | 50-mer 100 µM glycerol | 50-mer 100 µM glycerol | 50-mer 100 µM glycerol | 50-mer 100 µM glycerol | 50-mer 25 µM glycerol | 50-mer 25 µM glycerol |
| OligoT | 50-mer 25 µM G-PD | 50-mer 25 µM G-PD | 50-mer 25 µM G-PD | 50-mer 25 µM G-PD | 50-mer 100 µM G-PD | 50-mer 100 µM G-PD |
| OligoT | 50-mer 100 µM trehalose | 50-mer 100 µM trehalose | 50-mer 100 µM trehalose | 50-mer 100 µM trehalose | 50-mer 25 µM trehalose | 50-mer 25 µM trehalose |
| OligoT | 50-mer 25 µM G-S | 50-mer 25 µM G-S | 50-mer 25 µM G-S | 50-mer 25 µM G-S | 50-mer control | 50-mer control |

Right 6 × 13 segment of 12 × 12 Microarray

| [BSA] conc | 50 µg/ml | 20 µg/ml | 250 µg/ml | 100 µg/ml | 50 µg/ml | 20 µg/ml |
|---|---|---|---|---|---|---|
| OligoT | 50-mer 25 µM glycerol | 50-mer 25 µM glycerol | 50-mer 100 µM G-PD | 50-mer 100 µM G-PD | 50-mer 100 µM G-PD | 50-mer 100 µM G-PD |
| OligoT | 50-mer 100 µM PD | 50-mer 100 µM PD | 50-mer 25 µM PD | 50-mer 25 µM PD | 50-mer 25 µM PD | 50-mer 25 µM PD |
| OligoT | 50-mer 25 µM trehalose | 50-mer 25 µM trehalose | 50-mer 100 µM G-S | 50-mer 100 µM G-S | 50-mer 100 µM G-S | 50-mer 100 µM G-S |
| OligoT | | | | | | |
| OligoT | 50-mer 25 µM glycerol | 50-mer 25 µM glycerol | 50-mer 100 µM G-PD | 50-mer 100 µM G-PD | 50-mer 100 µM G-PD | 50-mer 100 µM G-PD |
| OligoT | 50-mer 100 µM PD | 50-mer 100 µM PD | 50-mer 25 µM PD | 50-mer 25 µM PD | 50-mer 25 µM PD | 50-mer 25 µM PD |
| OligoT | 50-mer 25 µM trehalose | 50-mer 25 µM trehalose | 50-mer 100 µM G-S | 50-mer 100 µM G-S | 50-mer 100 µM G-S | 50-mer 100 µM G-S |
| OligoT | | | | | | |
| OligoT | 50-mer 25 µM glycerol | 50-mer 25 µM glycerol | 50-mer 100 µM G-PD | 50-mer 100 µM G-PD | 50-mer 100 µM G-PD | 50-mer 100 µM G-PD |
| OligoT | 50-mer 100 µM PD | 50-mer 100 µM PD | 50-mer 25 µM PD | 50-mer 25 µM PD | 50-mer 25 µM PD | 50-mer 25 µM PD |
| OligoT | 50-mer 25 µM trehalose | 50-mer 25 µM trehalose | 50-mer 100 µM G-S | 50-mer 100 µM G-S | 50-mer 100 µM G-S | 50-mer 100 µM G-S |
| OligoT | | | | | | |

To the combination of BSA and Oligo-dT was added any one of a number of non-volatile, non-aqueous solvents and solutes including glycerol (G), glycerol-propanediol (GP) trehalose (T) and glycerol-sorbitol (GS). The resulting solution was printed onto either amino-silane coated or epoxysilane coated glass microarray substrates, using contact printing to form 100 um diameter spots, roughly 200 um on center. The print volume (@500 pL) was found to air-dry within 10 min, as assessed by fluorescent imaging of the microarray surface (Axon Imager).

Subsequent to air drying, the microarrays were crosslinked by exposure to 300 mJ of UV light (Stratolinker) to induce thymidine photochemical crosslinking via the thymidine moieties of the Oligo-dT. Subsequent to crosslinking, the slides were subjected to two 5 minute washing steps with a Tween 20 containing buffer, followed by administration of SAPE, to bind to the biotinylated BSA, so that it may be localized and quantitated by fluorescent imaging. In some cases, the SAPE staining was performed with 1% casein in the SAPE binding buffer, to provide for additional blocking of spurious SAPE binding to regions not modified with BSA. Subsequent to completion of the binding step (performed at room temp) a series of washes in protein free binding buffer and two water washes were performed (also at Room Temp) followed by air drying and imaging on an Axon laser scanner: at 532 nm (green for SAPE) and 635 nm (red, for Cy-5 labelled Oligo-dT).

A microarray design was used which presented various combinations of BSA, Oligo-dT and non-aqueous solvent and solute concentration (Table III). Representative images obtained of those microarrays, after binding and washing are presented in FIG. 2A (formed on an amino silane surface) or in FIG. 2B (formed on an epoxysilane surface).

As can be seen from the (red) CY-5 labelled Oligo-dT images the microarray printing and UV crosslinking procedure has permanently linked the Oligo-dT complement to the microarray surface on both an underlying aminosilane (FIG. 2A) and epoxysilane surface (FIG. 2B). As seen from the corresponding images generated via SAPE staining of biotinylated BSA (FIGS. 2A-2B, Right panels) the microarray printing and UV crosslinking procedure has also permanently linked the BSA protein to the surface, so that it may bind to SAPE.

Figure 3:
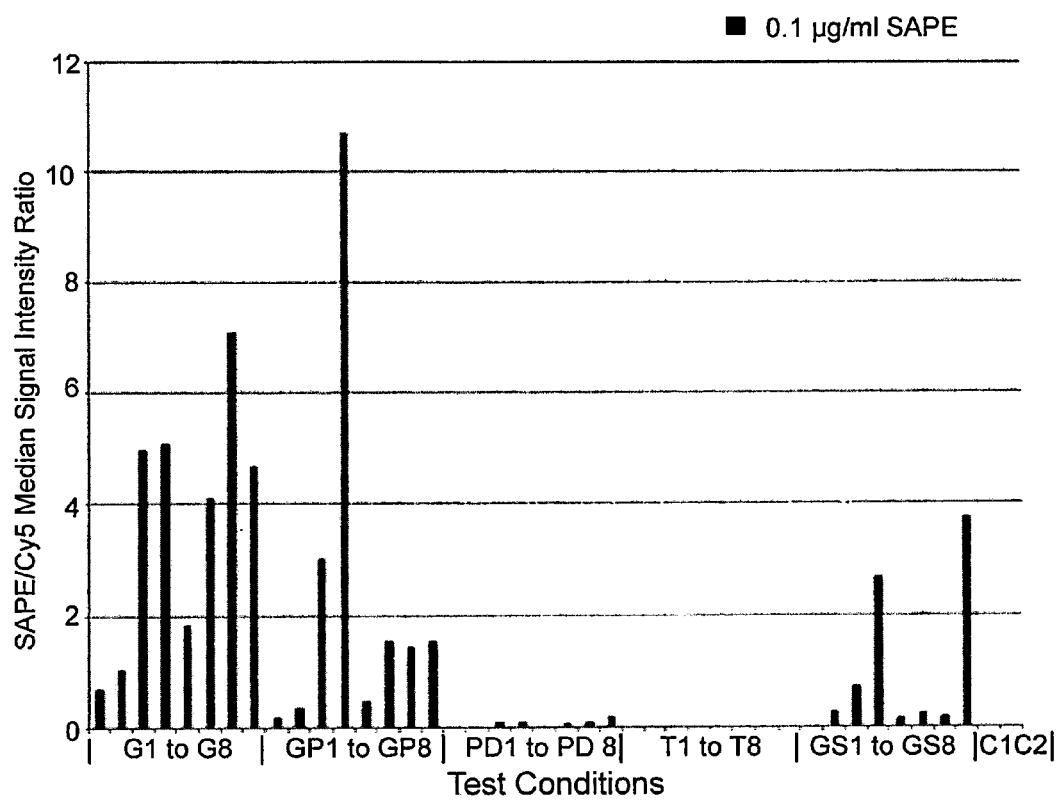
FIG. 3 depicts SAPE (Cy-3) signals normalized to OligoT (Cy-5) signals from a BSA microarray printed on an amino silane microarray surface, as in FIG. 2A.
Figure 4:
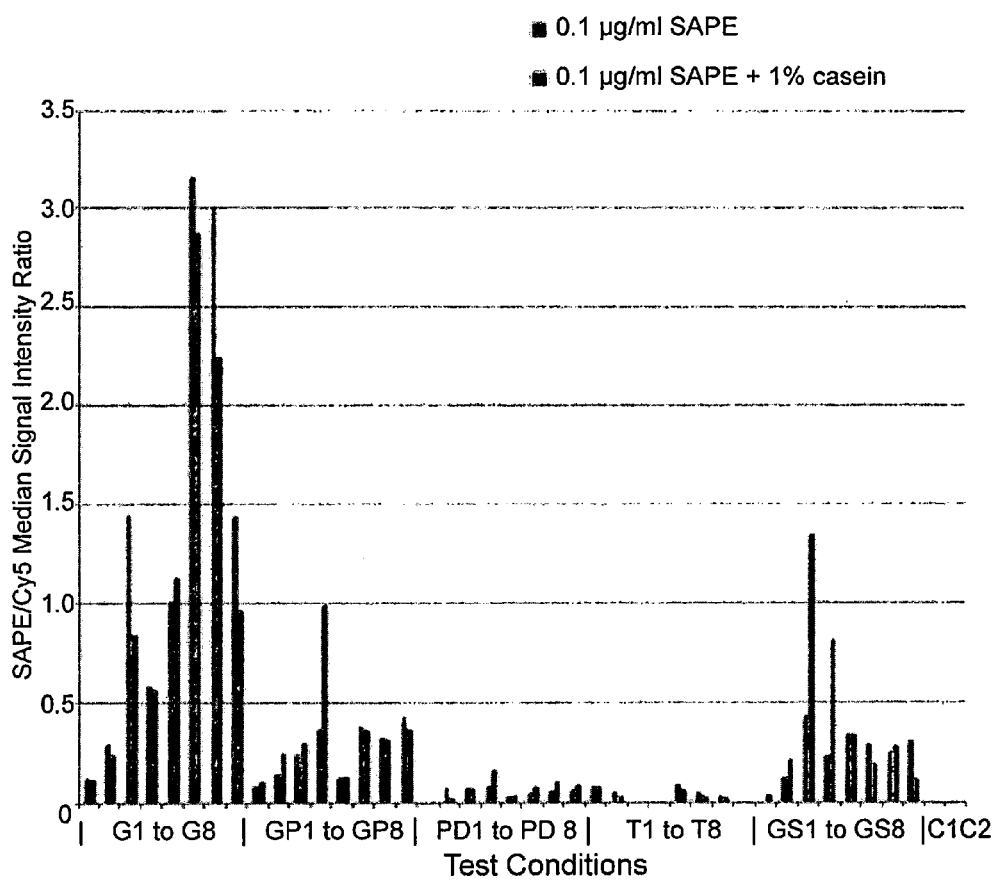
FIG. 4 depicts SAPE (Cy-3) signals normalized to OligoT (Cy-5) signals from a BSA microarray printed on an epoxy silane microarray surface, as in FIG. 2B.

Those image data have been quantified spot by spot and presented in FIG. 3 and FIG. 4 as the ratio of SAPE/Cy5 signal intensity, which is a measure of the ratio of BSA to Oligo-dT in each spot, as a function of variation in the several parameters described in Table III. FIG. 3 describes those ratios when the microarray is printed upon the aminosilane coated microarray substrate and FIG. 4 the corresponding data on the epoxysilane coated microarray substrate. Table IV provides the test conditions under which the ratios in FIGS. 3 and 4 were obtained. In Tables Va, Vb and Vc the numerical values used to generate FIGS. 3 and 4 are provided.

TABLE IV

| Adjuvant | Abbreviation | Sodium Phosphate pH 8.4 (mM) | Biotinylated BSA (μg/ml) | 50 mer Oligo-T (μM) | Cy5 Oligo-T (μM) |
| --- | --- | --- | --- | --- | --- |
| Glycerol 1% | G1 | 2 | 250 | 100 | 1 |
| | G2 | 2 | 100 | 100 | 1 |
| | G3 | 2 | 50 | 100 | 1 |
| | G4 | 2 | 20 | 100 | 1 |
| | G5 | 2 | 250 | 25 | 1 |
| | G6 | 2 | 100 | 25 | 1 |
| | G7 | 2 | 50 | 25 | 1 |
| | G8 | 2 | 20 | 25 | 1 |
| Glycerol-Propanedio 0.5%-0.5% | GP1 | 2 | 250 | 100 | 1 |
| | GP2 | 2 | 100 | 100 | 1 |
| | GP3 | 2 | 50 | 100 | 1 |
| | GP4 | 2 | 20 | 100 | 1 |
| | GP5 | 2 | 250 | 25 | 1 |
| | GP6 | 2 | 100 | 25 | 1 |
| | GP7 | 2 | 50 | 25 | 1 |
| | GP8 | 2 | 20 | 25 | 1 |
| Propanediol 1% | PD1 | 2 | 250 | 100 | 1 |
| | PD2 | 2 | 100 | 100 | 1 |
| | PD3 | 2 | 50 | 100 | 1 |
| | PD4 | 2 | 20 | 100 | 1 |
| | PD5 | 2 | 250 | 25 | 1 |
| | PD6 | 2 | 100 | 25 | 1 |
| | PD7 | 2 | 50 | 25 | 1 |
| | PD8 | 2 | 20 | 25 | 1 |
| Trehalose 1% | T1 | 2 | 250 | 100 | 1 |
| | T2 | 2 | 100 | 100 | 1 |
| | T3 | 2 | 50 | 100 | 1 |
| | T4 | 2 | 20 | 100 | 1 |
| | T5 | 2 | 250 | 25 | 1 |
| | T6 | 2 | 100 | 25 | 1 |
| | T7 | 2 | 50 | 25 | 1 |
| | T8 | 2 | 20 | 25 | 1 |
| Glycerol-Sorbitol 0.5%-0.5% | GS1 | 2 | 250 | 100 | 1 |
| | GS2 | 2 | 100 | 100 | 1 |
| | GS3 | 2 | 50 | 100 | 1 |
| | GS4 | 2 | 20 | 100 | 1 |
| | GS5 | 2 | 250 | 25 | 1 |
| | GS6 | 2 | 100 | 25 | 1 |
| | GS7 | 2 | 50 | 25 | 1 |
| | GS8 | 2 | 20 | 25 | 1 |
| Control | C1 | 150 | 250 | 0 | 1 |
| Trehalose 0.5% | C2 | 150 | 250 | 100 | 1 |

TABLE Va

| | SAPE @ 0.1 μg/ml | | | | |
| --- | --- | --- | --- | --- | --- |
| Test Condition | 635 nm Signal Intensity Post Printing | 635 nm Signal Intensity Post SAPE binding | Signal Decrease (%) | 532 nm SAPE Signal Intensity | SAPE/Cy5 Signal Intensity Ratio |
| G1 | 16955 | 9416 | 44 | 1206 | 0.13 |
| G2 | 6330 | 4121 | 35 | 1206 | 0.29 |
| G3 | 1037 | 753 | 27 | 1092 | 1.45 |
| G4 | 1939 | 1665 | 14 | 970 | 0.58 |
| G5 | 1832 | 991 | 46 | 1002 | 1.01 |
| G6 | 534 | 337 | 37 | 1066 | 3.16 |
| G7 | 504 | 366 | 27 | 1104 | 3.02 |
| G8 | 254 | 138 | 46 | 199 | 1.44 |
| GP1 | 22508 | 13284 | 41 | 1110 | 0.08 |

TABLE Va-continued

SAPE @ 0.1 μg/ml

| Test Condition | 635 nm Signal Intensity Post Printing | 635 nm Signal Intensity Post SAPE binding | Signal Decrease (%) | 532 nm SAPE Signal Intensity | SAPE/Cy5 Signal Intensity Ratio |
|---|---|---|---|---|---|
| GP2 | 11357 | 7742 | 32 | 1067 | 0.14 |
| GP3 | 6701 | 4608 | 31 | 1109 | 0.24 |
| GP4 | 572 | 567 | 1 | 208 | 0.37 |
| GP5 | 16316 | 7741 | 53 | 975 | 0.13 |
| GP6 | 5105 | 2814 | 45 | 1072 | 0.38 |
| GP7 | 5534 | 3356 | 39 | 1088 | 0.32 |
| GP8 | 2547 | 2142 | 16 | 935 | 0.44 |
| PD1 | 65535 | 62387 | 5 | 903 | 0.01 |
| PD2 | 37757 | 13239 | 65 | 949 | 0.07 |
| PD3 | 25895 | 8991 | 65 | 671 | 0.07 |
| PD4 | 7542 | 4459 | 41 | 377 | 0.08 |
| PD5 | 52806 | 26927 | 49 | 796 | 0.03 |
| PD6 | 43311 | 15303 | 65 | 810 | 0.05 |
| PD7 | 33466 | 17870 | 47 | 972 | 0.05 |
| PD8 | 35202 | 14819 | 58 | 952 | 0.06 |
| T1 | 65535 | 9356 | 86 | 805 | 0.09 |
| T2 | 65535 | 16762 | 74 | 974 | 0.06 |
| T3 | 65535 | 20414 | 69 | 423 | 0.02 |
| T4 | 65535 | 30171 | 54 | 353 | 0.01 |
| T5 | 65535 | 10151 | 85 | 930 | 0.09 |
| T6 | 65535 | 20582 | 69 | 991 | 0.05 |
| T7 | 65535 | 32239 | 51 | 991 | 0.03 |
| T8 | 65535 | 36545 | 44 | 631 | 0.02 |
| GS1 | 65535 | 38155 | 42 | 761 | 0.02 |
| GS2 | 11220 | 5398 | 52 | 696 | 0.13 |
| GS3 | 2844 | 1649 | 42 | 711 | 0.43 |
| GS4 | 5606 | 3358 | 40 | 779 | 0.23 |
| GS5 | 32347 | 2626 | 92 | 907 | 0.35 |
| GS6 | 7226 | 2089 | 71 | 605 | 0.29 |
| GS7 | 5039 | 1391 | 72 | 344 | 0.25 |
| GS8 | 3797 | 1475 | 61 | 451 | 0.31 |
| C1 | 65535 | 65535 | 0 | 730 | 0.01 |
| C2 | 65535 | 65535 | 0 | 609 | 0.01 |

TABLE Va

SAPE @ 0.1 μg/ml + 1% casein

| Test Condition | 635 nm Signal Intensity Post Printing | 635 nm Signal Intensity Post SAPE binding | Signal Decrease (%) | 532 nm SAPE Signal Intensity | SAPE/Cy5 Signal Intensity Ratio |
|---|---|---|---|---|---|
| G1 | 12131 | 7829 | 35 | 924 | 0.12 |
| G2 | 5625 | 3932 | 30 | 961 | 0.24 |
| G3 | 1081 | 891 | 18 | 749 | 0.84 |
| G4 | 1150 | 1140 | 1 | 647 | 0.57 |
| G5 | 1326 | 822 | 38 | 937 | 1.14 |
| G6 | 501 | 372 | 26 | 1071 | 2.88 |
| G7 | 611 | 480 | 21 | 1077 | 2.24 |
| G8 | 150 | 139 | 7 | 135 | 0.97 |
| GP1 | 15734 | 10458 | 34 | 1177 | 0.11 |
| GP2 | 7716 | 5523 | 28 | 1398 | 0.25 |
| GP3 | 6435 | 4714 | 27 | 1415 | 0.30 |
| GP4 | 137 | 124 | 9 | 123 | 0.99 |
| GP5 | 12493 | 6449 | 48 | 867 | 0.13 |
| GP6 | 3741 | 2450 | 35 | 909 | 0.37 |
| GP7 | 3796 | 2701 | 29 | 859 | 0.32 |
| GP8 | 3034 | 2173 | 28 | 791 | 0.36 |
| PD1 | 65535 | 65535 | 0 | 835 | 0.01 |
| PD2 | 49436 | 40764 | 18 | 847 | 0.02 |
| PD3 | 15169 | 8673 | 43 | 665 | 0.08 |
| PD4 | 3159 | 2420 | 23 | 401 | 0.17 |
| PD5 | 50343 | 30750 | 39 | 1201 | 0.04 |
| PD6 | 35607 | 14057 | 61 | 1227 | 0.09 |
| PD7 | 18201 | 9594 | 47 | 1072 | 0.11 |
| PD8 | 21455 | 10282 | 52 | 940 | 0.09 |
| T1 | 65535 | 9538 | 85 | 799 | 0.08 |
| T2 | 65535 | 15743 | 76 | 559 | 0.04 |
| T3 | 65535 | 17025 | 74 | 193 | 0.01 |
| T4 | 65535 | 19488 | 70 | 381 | 0.02 |

TABLE Va-continued

SAPE @ 0.1 µg/ml + 1% casein

| Test Condition | 635 nm Signal Intensity Post Printing | 635 nm Signal Intensity Post SAPE binding | Signal Decrease (%) | 532 nm SAPE Signal Intensity | SAPE/Cy5 Signal Intensity Ratio |
|---|---|---|---|---|---|
| T5 | 65535 | 9878 | 85 | 657 | 0.07 |
| T6 | 65535 | 17010 | 74 | 573 | 0.03 |
| T7 | 65535 | 24874 | 62 | 662 | 0.03 |
| T8 | 65535 | 31337 | 52 | 376 | 0.01 |
| GS1 | 64880 | 25578 | 61 | 1071 | 0.04 |
| GS2 | 10017 | 5088 | 49 | 1120 | 0.22 |
| GS3 | 1718 | 824 | 52 | 1112 | 1.35 |
| GS4 | 2662 | 1400 | 47 | 1143 | 0.82 |
| GS5 | 23631 | 2382 | 90 | 814 | 0.34 |
| GS6 | 6148 | 2138 | 65 | 412 | 0.19 |
| GS7 | 2023 | 686 | 66 | 193 | 0.28 |
| GS8 | 2577 | 1150 | 55 | 135 | 0.12 |
| C1 | 65535 | 65535 | 0 | 609 | 0.01 |
| C2 | 65535 | 65535 | 0 | 466 | 0.01 |

TABLE Vc

No SAPE

| Test Condition | 635 nm Signal Intensity Post Printing | 635 nm Signal Intensity Post SAPE binding | Signal Decrease (%) |
|---|---|---|---|
| G1 | 12204 | 7757 | 36 |
| G2 | 4491 | 3106 | 31 |
| G3 | 1123 | 881 | 22 |
| G4 | 1107 | 909 | 17 |
| G5 | 1164 | 747 | 36 |
| G6 | 471 | 349 | 26 |
| G7 | 526 | 388 | 26 |
| G8 | 149 | 115 | 23 |
| GP1 | 17385 | 11358 | 35 |
| GP2 | 8325 | 6067 | 27 |
| GP3 | 6290 | 4843 | 23 |
| GP4 | 158 | 143 | 9 |
| GP5 | 8795 | 5222 | 41 |
| GP6 | 3563 | 2312 | 35 |
| GP7 | 2999 | 2373 | 21 |
| GP8 | 3017 | 2260 | 25 |
| PD1 | 65535 | 65535 | 0 |
| PD2 | 65328 | 65202 | 0 |
| PD3 | 17243 | 13924 | 19 |
| PD4 | 1887 | 1389 | 26 |
| PD5 | 42002 | 31619 | 25 |
| PD6 | 29609 | 16240 | 45 |
| PD7 | 13903 | 6796 | 51 |
| PD8 | 22972 | 9982 | 57 |
| T1 | 65535 | 8988 | 86 |
| T2 | 65535 | 8687 | 87 |
| T3 | 65535 | 9271 | 86 |
| T4 | 58049 | 10853 | 81 |
| T5 | 65535 | 7114 | 89 |
| T6 | 65535 | 10515 | 84 |
| T7 | 65535 | 12761 | 81 |
| T8 | 65535 | 18387 | 72 |
| GS1 | 65535 | 25670 | 61 |
| GS2 | 10199 | 5146 | 50 |
| GS3 | 1652 | 789 | 52 |
| GS4 | 2339 | 1011 | 57 |
| GS5 | 21301 | 1977 | 91 |
| GS6 | 6112 | 1904 | 69 |
| GS7 | 2309 | 713 | 69 |
| GS8 | 1217 | 397 | 67 |
| C1 | 65535 | 65535 | 0 |
| C2 | 65535 | 65535 | 0 |

The trends obtained from FIGS. 3 and 4 are instructive. Overall, Oligo-dT crosslinking to permanently affix it onto the surface is efficient for both surfaces, more-less independent of the supporting non-aqueous solvent and solutes added. However, when the resulting SAPE/Cy-5 ratio was obtained, it was seen that glycerol (G) glycerol-propanediol (GP) and glycerol-sorbitol (GS) each provide for substantial biotin-BSA interaction with its cognate streptavidin-phycoerythrin (SAPE) conjugate. In contrast, it is seen that Trehalose (T) and to a lesser extent Propanediol (PD) provide for very poor BSA interaction due to poor protein association to the surface or protein disruption on the surface or both.

The above Examples demonstrate that Oligo-dT mediated UV crosslinking allows a protein such as BSA to be linked to a microarray surface to form, upon air-drying, a principally water free phase containing a number of nonvolatile water miscible solvents and solutes. The data show that, for BSA, certain solvent-solute pairs, e.g., glycerol and glycerol propane diol, appear to be superior to trehalose and propandiol in the present case of BSA attachment to the microarray surface.

What is claimed is:

1. A method of attaching a protein to a surface of a substrate, comprising the steps of:

printing one or more proteins; Oligo-dT; and one or more non-volatile, water-soluble protein solvents, solutes or combination thereof in an aqueous solution onto the substrate surface;

air-drying the substrate surface;

irradiating the substrate surface with UV light to induce thymidine photochemical crosslinking via the thymidine moieties of the Oligo-dT, thereby attaching the protein to the surface of the substrate.

* * * * *